(12) United States Patent
Gerde (10) Patent No.: US 8,555,873 B2
(45) Date of Patent: Oct. 15, 2013

(54) EXPOSURE SYSTEM

(75) Inventor: Per Gerde, Västerljung (SE)

(73) Assignee: Inhalation Sciences Sweden AB, Stockholm (SE)

(*) Notice: Subject to any disclaimer, the term of this patent is extended or adjusted under 35 U.S.C. 154(b) by 759 days.

(21) Appl. No.: 12/666,808

(22) PCT Filed: Jun. 27, 2008

(86) PCT No.: PCT/SE2008/050788
§ 371 (c)(1),
(2), (4) Date: Mar. 5, 2010

(87) PCT Pub. No.: WO2009/002267
PCT Pub. Date: Dec. 31, 2008

(65) Prior Publication Data
US 2011/0011160 A1    Jan. 20, 2011

Related U.S. Application Data

(60) Provisional application No. 61/040,336, filed on Mar. 28, 2008.

(30) Foreign Application Priority Data

Jun. 28, 2007  (SE) .................................... 0701569

(51) Int. Cl.
*A61M 11/00*    (2006.01)
(52) U.S. Cl.
USPC ............. 128/200.14; 128/203.15; 128/203.12
(58) Field of Classification Search
USPC ............. 128/200.14–200.24, 203.12, 204.18, 128/203.15, 203.21
See application file for complete search history.

(56) References Cited

U.S. PATENT DOCUMENTS 4,094,317 A * 6/1978 Wasnich .................. 128/200.16
4,819,629 A   4/1989 Jonson
(Continued)

FOREIGN PATENT DOCUMENTS

WO   95/16483 A1   6/1995
WO   96/00046 A1   1/1996
(Continued)

OTHER PUBLICATIONS

Gerde, "A Novel Method to Aerosolize Powder for Short Inhalation Exposures at High Concentrations: Isolated Rat Lungs Exposed to Respirable Diesel Soot," Inhalation Toxicology, 16(1):45-52 (2004).

*Primary Examiner* — Steven Douglas
(74) *Attorney, Agent, or Firm* — Porter Wright Morris & Arthur LLP (57) ABSTRACT

A system and a method for studying or predicting the interaction between a lung and an aerosolized agent. The system comprises an aerosol generator (10) sealingly connected to an exposure arrangement adapted to provide a transport aerosol flow from an aerosol holding chamber of the aerosol generator (10) to a flow junction; and an exposure aerosol flow from the flow junction for distribution to an exposure organ with breathing capacity thereby a providing a residual aerosol flow transported away from the flow junction. The exposure arrangement further comprises a flow rate monitoring device located upstream the flow junction for monitoring the transport aerosol flow, a device for measuring the aerosol particle concentration located downstream the flow rate monitoring device, and optionally a flow control function for controlling the transport aerosol flow. Using the system for predicting the interaction between a lung and an aerosolized agent minimizes the loss of the agent.

16 Claims, 8 Drawing Sheets

(56) References Cited

U.S. PATENT DOCUMENTS

| | | | |
|---|---|---|---|
| 5,458,135 A * | 10/1995 | Patton et al. | 128/200.14 |
| 6,003,512 A | 12/1999 | Gerde | |
| 6,269,810 B1 | 8/2001 | Brooker et al. | |
| 6,363,932 B1 * | 4/2002 | Forchione et al. | 128/203.12 |
| 6,854,460 B1 | 2/2005 | Shofner, II et al. | |
| 6,932,082 B2 * | 8/2005 | Stein | 128/200.22 |
| D605,283 S * | 12/2009 | White et al. | D24/110 |
| 8,001,962 B2 * | 8/2011 | Sheiman | 128/200.14 |
| 2004/0050966 A1 | 3/2004 | Piper | |
| 2005/0066968 A1 * | 3/2005 | Shofner et al. | 128/204.18 |
| 2006/0090752 A1 | 5/2006 | Imondi et al. | |

FOREIGN PATENT DOCUMENTS

| | | |
|---|---|---|
| WO | 00/51491 A1 | 9/2000 |
| WO | 02/02052 A2 | 1/2002 |

\* cited by examiner

EXPOSURE SYSTEM

RELATED APPLICATION

This application is a 371 of PCT/SE2008/050788 filed Jun. 27, 2008 and claims priority under 35 U.S.C. §119 of U.S. Application Ser. No. 61/040,336 filed Mar. 28, 2008.

FIELD OF INVENTION

The present invention relates to a system and methods for adapted to study or support the study of pulmonary uptake of an aerosolized agent.

BACKGROUND OF INVENTION

Inhalable aerosolized drugs for inhalation are generally considered as conceivable alternatives to injections or other types of drug-delivery systems, such as intravenous delivery, subcutaneous or intramuscular injections. For example, insulin is desirable to deliver by inhalation of an aerosolized form to improve patient compliance. It is, however, a general problem with inhalable aerosols that the delivered dose is inaccurate in comparison to injections and the correct amount required for delivery frequently is not properly metered for delivery. Both for systemic drug delivery and for screening of drugs with aerosol using pulmonary models, a low level of accuracy is a drawback for appropriate use both for a safe therapy or a resourceful screening model.

For the most part in the clinic, it is desirable to deliver a predetermined dose of drug with as short exposure time as possible—preferably a single-breath inhalation maneuver dispensing a well-controlled bolus of aerosolized drug at a high concentration to the respiratory tract. It would therefore be equally desirable to mimic this exposure strategy also in the early drug development process in order to collect as relevant data as possible. However, because of technical limitations in most aerosol generator technologies and delivery systems, this has rarely been achieved. Most available generator technologies have continuous outputs consuming large amounts of substance. It is the intent of the current invention to overcome this limitation and enable bolus type exposures to respirable aerosols also in early drug development.

U.S. Pat. No. 6,003,512 describes a dust gun aerosol generator and methods of aerosolizing and dispensing powders. This equipment provides inhalable aerosols with highly repeatable properties from small amounts of powders. The high deagglomeration power of the equipment provides for that diluents and excipients can be avoided and that a highly repeatable, suitably concentrated aerosol dose with homogenous particle size is generated even from small amounts of cohesive powders. Accordingly the dust gun aerosol generator has showed to be a useful tool to combine with an isolated, ventilated and perfused lung of rodents (IPL), as is disclosed in P Gerde et al. Inhalation Toxicology, 2004, 16, 45-52 wherein the pulmonary deposition of diesel soot was studied. U.S. Pat. No. 5,887,586 (Dahlbäck et al.) discloses a method and a system for measuring a dose inhaled by an animal from an aerosolized drug. The system comprises means for more accurately measuring the inhaled dose. It does however, suffer from a drawback in that the distance between the aerosol generator and the animal becomes rather long, resulting in a high dead space leading to significant losses of aerosolized drug in the system and in that a relatively high amount of drug never reaches the lungs of the animal. Loss of drug to deposition in equipment is highly unwanted, particularly in the early stage of drug candidate screening due to economic reasons. U.S. Pat. No. 6,269,810 describes a pulmonary dosing system and methods of its operation strictly for therapeutic purposes. The system depends only on filters for calibration, which is insufficient for an accurate estimation of the deposited to dose with respect to aerosol losses from aerosol generator to the exposure target necessary when for example evaluating the performance of drug candidates.

During inhalation exposures with drug substance candidates, deposition of a studied substance in the target region of the lungs is a desired process that is always accompanied by unwanted losses of study material through deposition in delivery equipment and in non-target regions of the respiratory tract. Early in the development process of drugs intended for inhalation delivery, substance loss is a critical factor preventing often decisive early tests via inhalation. Two major mechanisms lead to wall deposition of particles when an aerosol is flowing through a duct: aerodynamic losses and electrostatic losses. Aerodynamic losses are contributed by diffusion, sedimentation, impaction, and interception of particles and are influenced primarily by the mass median aerodynamic diameter (MMAD) of the studied aerosol and by the fluid dynamics of the duct system under study. Aerodynamic losses can be reasonably well predicted with theoretical models. Electrostatic losses are superimposed on the aerodynamic losses, and depend strongly on material properties of the studied powder and the walls of the duct system. Electrostatic losses are more erratic and difficult to predict, and can be the dominating deposition mechanism of a studied aerosol. This unpredictable behaviour of powder aerosols leads to substance losses not only to vessel walls of aerosol generator equipment, exposure systems, and to non-target regions of the respiratory tract, but also during the adjustment of exposure parameters needed to attain target exposures in study subjects. It is the intent of the current invention to address both these problems;

A specific problem with bolus type inhalation exposures is to control both the aerosol concentration and the duration of the aerosol presence in the inhaled gas. In the ideal situation, the aerosol is present at a predetermined concentration in the inhaled gas between time on and time off, determined by the breathing pattern of the exposure subject. The aerosol concentration should represent a square wave without dispersion or tailing in the end. However, this is difficult to accomplish and a typical concentration curve for an aerosol bolus is uneven and contains a longer tail of gradually decreasing concentration. One fundamental mechanism affecting aerosol boluses of dense aerosols is the cloud settling phenomenon (NA Fuchs, The Mechanics of Aerosols, Pergamon Press, Oxford UK, 1964). Dense aerosols with an average density that is only slightly higher than the surrounding air tend to move in separated clouds where the cloud moves faster than the individual particles relative to their surrounding gas matrix (see W C Hinds et al., Aerosol Science and Technology, Vol. 36, pp. 1128-1138, 2002). Cloud settling can be a major factor contributing to an increased dispersion of an aerosol bolus, particularly of the terminating end of an aerosol exposure. Such dispersion can prevent substantial parts of an intended aerosol dose from reaching the target area of the respiratory tract or usually depositing instead in the exposure equipment or arriving in the target area outside the predetermined time window.

Intermittent, burst-type of aerosol generators such as the aforementioned dust gun or the Exubera® (Pfizer Inc.) eject a plume of aerosol into a more or less stagnant medium. The kinetic energy of the deagglomerating burst quickly dissipates, and a characteristic plume is formed. Subsequently, the plume will be affected by diffusional, convective, and gravitational forces that will disperse and dilute the aerosol of the plume. For inhalation exposures it is most often a desire to convert the burst plume into an aerosol bolus to be inhaled by an exposure subject in one or several breaths. The aerosol bolus should present a step increase in aerosol concentration from zero to a constant level and remain level until the bolus ends with a step decrease to zero from the average concentration. Ideally the bolus average concentration should be the amount of substance loaded and aerosolized divided by the bolus volume Thus, a need exists for accurately and predictably delivering a predetermined dose of aerosolized drugs with minimized substance losses in the equipment and to reach target dose without any range-finding exposures with tissues or animals. There is also a need for a system that allows for accurate testing of aersoslizable drug candidates in very early stage when only small amounts of substances are available. For these purposes, an exposure system has been assembled by connecting the aerosol generator through a manifold arrangement with an isolated perfused lung or with the respiratory tract of intact animals. It is apparent that the mentioned exposure system including the dust gun aerosol generator can be efficiently employed when screening and evaluating new drug candidates for local action in the lungs or for systemic uptake through pulmonary administration. Especially, the dust gun system can be part of an arrangement and a methodology, which greatly reduces quantities and pre-processing of synthesized drugs, simplifies the screening process, while reducing the employment of biological material including test animals. The invention as described in the following sections is adapted to meet such requirements.

SUMMARY OF THE INVENTION

It is first object of the present invention to provide a model that supports prediction of how candidate substances for subsequent drug development depose, absorb and metabolise following pulmonary administration.

It is a further object of the present invention is to provide for a system which is equally useful for estimating or predicting a deposited dose of an aerosol when the tissue-retained fraction of substance cannot be measured, or for further pharmacokinetic modeling with tissues or test animals.

It is a still further object of the present invention to provide for that a minimum of losses of the dispensed dose of aerosolized drug in the equipment, outside the exposure subject, and to allow for recovery of equipment-deposited material after the exposure series.

Another important object of the present invention is to provide for a methodology of screening drug candidates wherein the performances can be directed to aerosol exposures with small amount of substances while reducing the involvement of biological tissue and test animals These objects are achieved by the systems of the present invention generally relating to an aerosol generator together with an exposure arrangement and the methods for determining a dose delivered to a lung from collecting aerosol particles in the system. The systems and the methods are further defined in the appended section containing the specification including the appended claims.

DESCRIPTION OF THE INVENTION

In the most general terms, the present invention relates to a system suitable for studying or predicting the interaction between a lung and an aerosolized agent comprising an aerosol generator sealingly connected to an exposure arrangement. The system is adapted to collect a portion of periodically generated aerosol from an intermittent aerosol generator in a suitable aerosol holding chamber, then provide a transport aerosol flow from the aerosol holding chamber of the aerosol generator to a flow junction and to provide an exposure aerosol flow from the flow junction for distribution to an exposure organ with breathing capacity Thereby a residual aerosol flow is provided, which is transported away from the flow junction. The exposure arrangement also comprises a flow control function for controlling the transport aerosol flow, which in this context means the function both may comprise means for generating a predetermined flow and for controlling the direction of the flow. The exposure arrangement further comprises a flow rate monitoring device located upstream the flow junction for monitoring the transport aerosol flow and a device for measuring the aerosol particle concentration located downstream the flow rate monitoring device. Also in a general sense, the system is adaptable for studying or predicting the interaction between an aerosolized agent and differently sized lungs. The volume of aerosol holding chamber is then adapted to an estimated lung volume of the exposure organ in order to fall within one of three exposure scenarios to be described.

It is to be understood that the system includes a number of conduits adapted for sealed transportation of the aerosol from the generator to the exposure organ. In this context, the person skilled in the art understands to select and assemble conduits to minimize loss of aerosol due to unnecessary extensions, pockets or other trappings for particles.

When describing the system and its different parts or constituents, the terms "distal" and "proximal" will be used herein. It should be understood the distal end of the system is the part where the aerosol is generated and the proximal end is the part where the interaction between the aerosol and the deposition organ is studied. Accordingly the terms distal and proximal is used to define the position in the system relative to the two mentioned functional parts.

The term "aerosol" is frequently referred to as a mist of liquid droplets; however term as used in the present context refers to a suspension of solid particles in airflow. Accordingly the term "aerosol" can also mean an "aerosol bolus" describing a volume of air with suspended particles of a formulation. The air volume may by way of example vary between about 3 ml to less than about 4 liters, while the particles may have diameter of preferably about 0.1 to 10 microns The terms "aerosol," "particles," "aerosol particles," "aerosolized formulation" and similar are used interchangeably in the present context and will refer to particles of formulation comprised of pharmaceutically active drug and carrier which are formed for aerosol delivery.

The deposition organ is understood to be widely defined as an organ interacting with the aerosol, at which, or wherein particles of the aerosol are deposited, i.e. a fraction of the totally administered aerosol dose interacting with the deposition organ. In the context of the present invention, a deposition organ can be an isolated ventilated and perfused lung, the lung of a test animal connected to the system, with a nose mask or intratracheal catheter, or an inhalation filter adapted to interact with the aerosol. The terms "exposure target" or "exposure organ" are also used in the context of present invention and should be regarded to have the similar general meaning as "deposition organ" namely target for the aerosol delivery with inventive system and methods.

In one embodiment, the present invention relates to the previously described system adapted for predicting the dose of an aerosolized agent to be deposited in an isolated, ventilated and perfused lung or the lung of a test animal. According to this embodiment, the exposure aerosol flow is sealingly directed from the junction to an exposure organ comprising an inhalation filter provided in a housing adapted to establish a controlled exposure of the exposure organ to the aerosol. The inhalation filter is connected to a breathing simulator adapted to perform the breathing pattern of a test animal. It will be described how the system can be readily adapted to perform different breathing capacities. Further in this embodiment the flow control function provides a controlled flow rate of transport aerosol flow between the aerosol holding chamber and the junction point and in one preferred aspect, the flow control function is vacuum source located downstream the flow junction. During certain circumstances it is preferred that the flow control function comprises one or several flow direction controlling devices in order to ensure that the direction of transport flow is correct. Still further, the system of this embodiment has an aerosol inlet device sealingly connected to the housing lid part and provided with a generally tubular channel for distributing the transport aerosol to the flow junction; and a filter device provided with a generally tubular channel connected to the flow junction to receive a residual aerosol flow and a downstream filter chamber provided with a detachable filter holder for an aerosol residual filter. Preferably, the tubular channel of the aerosol inlet device extends in an angle not exceeding 45 degrees from the essentially horizontal plane of the residual filter on which residual aerosol particles deposit and is retained by gravity. This arrangement avoids particle losses by gravity from heavily coated filters. The inhalation filter of the system has a distal part attachable to the connecting means to a lid of said housing and a proximal part connected to a releasable filter holder comprising a deposition filter. A filter conduit extends between said proximal and distal parts with an extension substantially corresponding to the extension of the conduit between the flow junction and the exposure subject. It is preferable that the filter conduit and said tubular channel of the aerosol inlet device are located at an angle of about 45 degrees. It is also preferable that the flow control function is a vacuum source located downstream of the filter device.

In one aspect of the discussed embodiment the system is operated with a transport aerosol flow that is higher than exhalation breathing flow capacity generated by the breathing simulator. This is would also generally be the case with test animals having small lung capacity.

In other aspect of the discussed embodiment, the system is operated with an exhalation breathing flow capacity exceeding the transport aerosol flow, which will apply to a test animal with a medium sized lung. In this case, the flow control function preferably comprises a one-way valve located upstream of the flow monitoring device. Further, the transport aerosol flow can be supported with a ventilation balloon located upstream the flow monitoring device.

Whereas, the two mentioned aspects are related to conditions where small or medium sized lungs are considered, the discussed embodiment of the system can be adapted to conditions where large lungs (i.e. of larger animals such as dogs). In such a case, the breathing simulator operates with a tidal volume exceeding the volume of the aerosol holding chamber and wherein the flow control function includes at least two one-way valves. The large breathing capacity reduces the residual flow of aerosol and the system can be run in the absence of filter device connected to the flow junction. Instead, a one-way valve is positioned downstream the flow junction in the residual flow to ensure that no aerosol is lost during exhalations. Another one-way valve, preferably is located upstream the flow monitoring device and a ventilation balloon with the previously described function can be located between the one-way valve and the flow monitoring device.

While so far embodiments of the inventive system have been described which are adapted to predict how aerosol interacts with a deposition organ, the system can readily be run with an IPL or a test animal with essentially same features as described under essentially same conditions. However, instead of inhalation filter as described, the system now comprises connecting adaptations from the flow junction to either an IPL in a housing or a nose mask or tracheal catheter of a test animal.

Accordingly, to study the interaction between a lung with breathing capacity generating a tidal volume less than the volume of the aerosol holding chamber, the system comprises an exposure aerosol flow is sealingly directed from the junction; and a flow control function providing a controlled flow rate of transport aerosol flow between the aerosol holding chamber and the junction. The flow control function preferably is a vacuum source located downstream to the flow junction. In this case, the system can further comprise a filter device provided with a generally tubular channel connected to the flow junction to receive a residual aerosol flow and a downstream filter chamber provided with a detachable filter holder for an aerosol particle deposition filter.

In case the deposition organ is an IPL it is accommodated in a housing adapted to sealingly receive the exposure aerosol flow from the flow junction. Preferably, the IPL is perfused with perfusion fluid during the exposure cycle with the aerosol and for this purpose the housing is adapted to receive a flow of perfusion fluid and to with means to repeatedly collect perfusion fluid for analysis and study for example by being connected to a fluid fraction collector and suitable analytical devices. These parts may generally be regarded as a part of the exposure system, but since they do become a part of the present invention, they are not described further in this context.

When the deposition organ is the lung of a test animal, the system is adapted in a similar manner to the lung size, i.e. the breathing capacity of the animal as been earlier described. The animal is sealingly connected to the junction point to receive the exposure flow through a nose mask or a similar arrangement. For animals having an exhalation breathing flow capacity exceeding the transport aerosol flow, the flow control function further comprising a flow direction restriction device located upstream of the flow monitoring device. Preferably, the flow direction restriction device is a one-way valve and the flow control function can further comprise a ventilation balloon with capacity to enhance the transport aerosol flow.

For a large test animal with breathing capacity generating a tidal volume larger than the volume of the aerosol holding chamber the flow direction controlling devices comprises a first one-way valve located upstream of the flow monitoring device and a second one-way valve located downstream of the flow junction to control the direction of the residual flow and a ventilation balloon with capacity to enhance the transport aerosol flow can preferably be located between the upstream one-way valve and the flow monitoring device.

The aerosol generator of the system preferably comprises the use of a rapidly expanding pressurized gas for mixing with an enclosed powder dose and to deagglomerate the powder particles to an aerosol dispensable to said aerosol-holding chamber. A suitable such aerosol generator is disclosed in the aforementioned U.S. Pat. No. 6,003,512 and comprises, in order to aerosolize and dispense powders, a pressure chamber, at least one substantially straight ejecting conduit opening at an exit nozzle to ambient pressures, an enclosed powder chamber for loading with said pressurized gas and mixing the powder, and at least one pressure conduit connecting said pressure chamber and powder chamber. In this embodiment, the substantially circular exit nozzle has a substantially uniform cross-section opening, and preferably the ejecting conduit comprises a cylinder.

In an important embodiment of the present invention, the system design is adapted to the cloud settling phenomenon in order to minimize the loss of aerosol in chambers and conduits. It is the intent to exploit the cloud settling phenomenon in order to (1) maintain the initial concentration of the intermittently generated bursts of aerosol as constant as possible, (2) dispense the generated aerosol bolus to the exposure subject in portions or as a whole with a minimum dispersion or backmixing at the leading or trailing ends of the desired bolus, and (3), to minimize aerosol losses to the vessel walls of the aerosol equipment and to allow for recovery of equipment-deposited material. For this purpose the previously described systems can comprise a generally conically shaped aerosol holding chamber which vertically extends between a bottom part and a top part. The top part has a larger crossectional area than the bottom part giving the holding chamber the general shape of inverted cone adapted to conform with a generally cone-shaped aerosol burst from the aerosol generator following the lower boundary of the burst cloud. The bottom part of the holding chamber has an aerosol inlet adapted to receive an upwardly directed burst of an aerosol bolus from the aerosol generator. Further, the holding chamber comprises an outlet conduit in its bottom part for downstream transportation of the aerosol to an exposure target. Preferably, the outlet conduit is downwardly directed. It is suitable that the outlet conduit has downward direction such that a plane cutting the conduit longitudinally and symmetrically has an angle to a horizontal plane of about thirty degrees in order to support further transportation of the aerosol in the system. The top part of aerosol holding chamber can be provided with a diffuser for aerosol particle-free inlet air for introducing a clean air layer over the introduced aerosol.

The present invention also relates to novel method of transporting aerosol in an aerosol bolus to an exposure target with even concentration and minimized losses. The method generally comprises the steps of introducing an upwardly directed burst of aerosol from the aerosol generator in the bottom part of a generally vertically oriented holding chamber having the shape of an inverted cone; allowing the aerosol to settle as a cloud and increase in density by means of gravitation in said holding chamber; introducing a layer of lighter clean air over said denser aerosol cloud; and receiving an aerosol stream in a downwardly directed outlet conduit of the holding chamber for transportation to the exposure target. The method is preferably performed while preventing unstable mixing of the aerosol and the clean air. Preferably, the aerosol is admitted to settle in the holding chamber under the influence of gravitation, while the initially kinetic energy of the burst from the generator dissipates. During this process, it is preferred that the aerosol cloud reaches a stable boundary towards the above laying introduced lighter clean air. The aerosol will increase in density during the settling and it is generally considered that a critical density increase in the region of 0.1% (wt) is suitable to reach for a transportation meeting the objectives of the invention. An outlet conduit located in a bottom part of the holding chamber will receive the aerosol for further transportation to a target. In one example the transportation is performed by gravitation in a downwardly directed system. When performing the transportation method, the clean air can be arranged to exert a pressure on the aerosol cloud, thereby supporting its displacement from the holding chamber.

In order to comply with the described transportation method an aerosol holding chamber for accommodation of an aerosol burst and transportation of an aerosol to an exposure target is arranged with an essentially vertical chamber extended between a top part and a bottom part having a top part with a larger crossectional area than the bottom part. The chamber thereby obtains the general configuration of an inverted cone with a bottom part provided with an aerosol inlet adapted to receive an upwardly directed burst of an aerosol bolus from the aerosol generator and an aerosol outlet conduit for receiving the aerosol for transportation to the exposure target. The chamber can be arranged with a valve function for opening the outlet conduit for transportation and the outlet conduit, preferably is downwardly directed. Further, the chamber is arranged with a diffuser located in the top part for introducing clean particle-free air as a stable layer on top of the denser aerosol.

The described method and arrangement for aerosol transportation enable the conversion of an aerosol generator burst into an aerosol bolus of desired concentration with minimal deviation form an ideal square-wave shape and with as little loss of material as possible. For this purpose, the holding chamber and exposure conduit are designed to minimize the dispersion or smearing-out of intermittent aerosol boli that is likely to be caused both by the cloud-settling phenomenon or Rayleigh-Taylor instabilities, and by aerodynamic and electrostatic mechanisms. For denser aerosols the most important mechanism causing dispersion is the cloud settling phenomenon.

The present invention intends to remedy dispersion driven by cloud settling. Dense aerosol bursts from the aerosol generator must settle with gravity into a stable configuration as quickly as possible in order to present a distinct step in the concentration at the leading edge of the aerosol bolus. For cone-shaped bursts from the generator it is suggested to arrange a similar-shaped inverted cone following the lower boundary of the burst cloud. As soon as the kinetic energy of the burst has dissipated, the aerosol quickly settles into a stable bolus in the conical holding chamber and upon removal from the holding chamber, the aerosol will quickly attain a high and constant concentration. In order to minimize dispersion at the trailing edge of the bolus, the aerosol bolus is displaced by layering a lighter aerosol-free gas on top of the denser aerosol bolus. It is also an advantage to maintain a downward slope on the exposure conduit as close as possible to the exposure subject. As a result, a dense aerosol is extracted from the holding chamber as a well-defined bolus with little dispersion toward the trailing end. When a diffuser-type device is used to layer the particle-free air on top, the duration of the elevated aerosol concentration in the exposure stream will be close to the void time of that stream in the holding chamber, and the aerosol concentration will be close to the amount of powder ejected from the aerosol generator divided with the holding chamber volume. It is generally observed that the Rayleigh-Taylor instabilities will contribute more to increased dispersion the higher the aerosol concentration and the lower the flow rate through the system. In summary, the described improvements in aerosol transportation surprisingly decreases losses of material while admitting the generation of well-defined aerosol bolus to be received by a target to be exposed to aerosol. These findings represent significant improvements for many applications where dosage inaccuracy has been problem as exemplified, but not limited to aerosol drug delivery in therapy.

In another embodiment, the inventive system can be employed to a method of determining the amount agent absorbed by the lungs in test model with an IPL, wherein an exposure cycle with an aerosol dose is performed, while perfusing the IPL with perfusion fluid in a single-pass mode and sampling perfusion fluid downstream the IPL during the exposure sequence with predetermined durations. Each sample is weighed and by determining the perfusate flow rate solute absorption from the lungs is calculated. Provided the hydrostatic pressure of the perfusate in the lungs is held constant, the measured flow rate can be used as a diagnostic instrument to measure the effects of different inhaled agents or drugs on the resistance in the pulmonary circulation following inhalation exposures with current exposure system.

In another embodiment, the invention refers to a method for predicting the pulmonary administered dose (or "projected deposition of active substance") to an IPL preferably by employing a previously described system comprising an inhalation filter in an aerosol exposure. The method comprises the provision of an aerosol from a dose of a powder formed agent with the aerosol generator and transporting the aerosol with the exposure arrangement to the inhalation filter connected to a breathing simulator with a predetermined tidal volume. In this method the values of the mass median aerodynamic diameter (MMAD) of the aerosol units, the mass value of aerosol particles deposited on the residual filter (Mres) and the mass value of aerosol deposited on the filter in the inhalation filter (Minh) are determined. The mass median aerodynamic diameter (MMAD) can, for example be measured by a cascade impactor device. From these values, the predicted pulmonary administered dose (Mdep) can be calculated. The method can further include a determination of the aerosol particle concentration in the aerosol inlet device, for example with an instrument determining the reflection and/or the scattering of light from the flowing aerosol particles, and the determination of the mass value (Mres) of aerosol particles deposited on a residual filter receiving the residual flow from flow junction. From the value of Mres the filter factor corrected aerosol particle concentration (Ccorr) can be determined. The predicted pulmonary administered dose (Mdep) can then be determined also from the breathing pattern of the exposure arrangement by employing the filter factor corrected aerosol particle concentration (Ccorr), the tidal volume (TV) of the breathing simulator and the fraction deposited aerosol with the measured mass median aerodynamic diameter (MMAD). Further features of the inventive method include a monitoring function of the aerosol flow rate at the inlet to the exposure arrangement and the provision for a constant or substantially constant aerosol transport flow rate. In order to avoid any re-breathing of exhausted exposure atmosphere, it is preferred that the exposure flow rate is to at least three times the ventilation of breathing simulator.

A particularly important embodiment the present invention relates to a method of screening drug candidates based on their interaction properties with lungs. Firstly, a powdered dose of a drug candidate is aerosolized with the system described above adapted to determine the predicted pulmonary deposited dose (Mdep) according to the previously described routines without using tissues or animals. Secondly, the predicted deposition of the powdered drug can now be used for running the system to expose a lung to the same aerosol for determining how the drug candidate interacts with lung tissue. In other terms the determining of the dose to deposited dose in the lung admits that the system can be run with an optimized exposure time and other operation conditions as previously described subsequent tests with test subjects which greatly optimizes conditions when low amounts of test material is available. The lung can be either an IPL or the lung of a test animal. Preferably the transport aerosol flow is kept essentially the same. Preferably and advantageously, small amounts of drugs in the mg scale are used, such as less than 100 mg. By following the outline of the method, the general advantages of the system in operating with optimized amounts of expensive material are further enhanced and quick, reliable discrimination between different drug candidates can effectively be performed at an early preclinical stage. Interaction studies made available with the method include not only absorption studies of the drug candidate, but is also equally feasible for studying a number of physiological effects including drug activity exerted in or via lung tissues, such as metabolism, pharmacological- and toxicological responses including onset of therapeutic action, as well as bioavailability and phamarcokinetic aspects. The presently invented system and the methodologies using the system will reduce and simplify the discovery and preclinical phases of drug development and thereby be of significant benefit to bring down the costs in an industry suffering from increasing burdens when attempting to find new original products for market approval. The system and the methods described are equally useful in diagnostic applications, wherein the described methodology can be applied of determining pulmonary deposition and determining airway sensitivity for an agent. The same benefits will be evident for a diagnostic application regarding low dosing and test accuracy.

Another important aspect of the current invention is the method of minimizing aerosol losses in the holding chamber and tubing by only allowing the aerosol to flow down with the gravitational gradient into the exposure subject. Flow with the gravitational gradient prevents Rayleigh-Taylor instabilities to cause unnecessary backmixing or dispersion of the aerosol bolus. Another method of minimizing substance loss is to allow for powder recovery from the holding chamber vessel walls. Wall-deposited powder can be recovered from the holding chamber walls by attaching the powder chamber with a rubber sealing on the lid of powder chamber and with a rubber clad seal at the top of the column. At the end of an exposure series with the same material the steeply inclined walls of the holding chamber are vibrated with a suitable device to allow loose powder to slide with gravity into a small metal foil pan place over the powder chamber lid. The metal pan can be easily removed after the exposures and the powder can be recovered.

The following detailed description shows a number of examples of the inventive system and its operation which are not intended to limit the scope of protection as outlined by the appended claims.

DETAILED DESCRIPTION OF THE INVENTION

Description of the Exposure System and a Work Cycle

Figure 1:
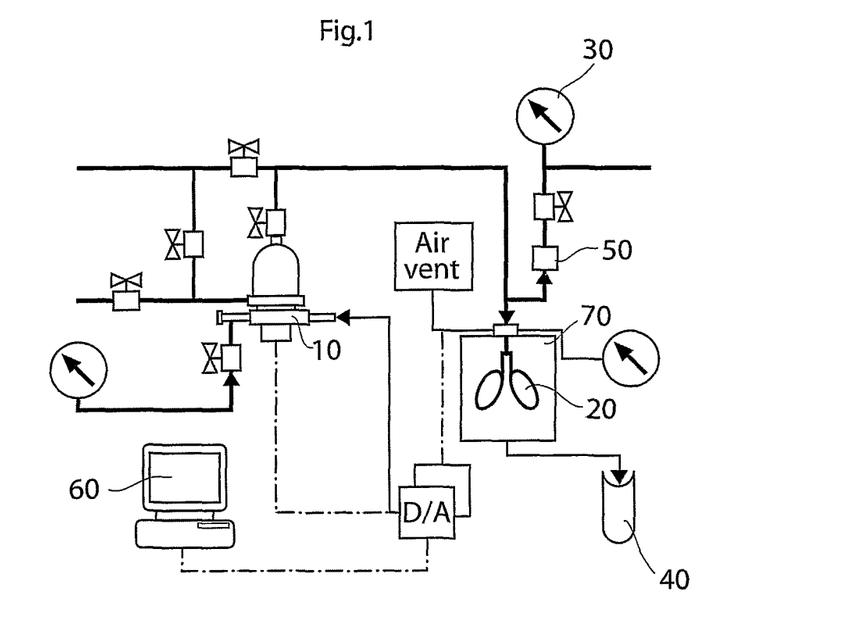
FIG. 1 shows a schematic overview of the system according to the invention.

Referring now to FIG. 1 a work cycle of the exposure system is described. FIG. 1 shows a system including an aerosol generator (10), integrated with a 300 ml holding chamber an exposure manifold arrangement to direct an regulate the duration of exposure and a computerized control system for automation and control of the exposures. The aerosol generator consists of three major components (not shown): a fixed volume powder chamber, a variable volume pressure chamber and fast releasing valve. For further details of the aerosol generator and its supporting equipment, it as also referred to P Gerde et al. Inhalation Toxicology, 2004, 16, 45-52 which is incorporated as a reference. For receiving the freshly generated aerosol, the powder chamber is connected to the holding chamber. The aerosol is delivered to the exposure subject (20) accommodated in the exposure housing (70) by means of a custom made exposure manifold with pneumatically activated pinch valves, designated V1, V2, V3 and V4 in FIG. 1, and an exposure line leading past the exposure subject (the tracheal cannula of the rat isolated perfused lung (IPL). A negative pressure, driving the exposure flow of aerosol past the exposure subject, is obtained by use of a precision controlled vacuum source (30). The aerosol cloud is drawn from the holding chamber with the precision controlled vacuum source to the aerosol inlet device (not shown) and an immediately downstream residual filter (50) (Waltham GF/A, UK). The residual filter (50) collects all aerosol that has either bypassed or been exhaled by the lungs. Particles deposited on the essentially horizontal residual filter will be retained by gravity. The exposure system can maintain an exposure to a bolus of aerosolized dry powders for approximately 1-2 minutes. The exposure housing includes a perfusion arrangement for perfusing the IPL and is connected to a fraction collector (40) for further study of the interaction between the IPL and the aerosol. The system is fully computer controlled with a LabView software package (60) on a lap top computer. The system monitors and records for use in the control system the pressure in the pressure chamber, the inlet flow rate to the exposure line, the particle concentration and the weights and time of duration of all perfused samples. The pressure in the pressure chamber is monitored during aerosol generation with a WIKA Microtronic pressure transducer. The pressure reading is used to a reset the main valve at any chosen remaining pressure in the pressure chamber. The function decreases the volume of driving gas added to the holding chamber during the late phase of decompression when little aerosol remains to be generated. The pressure recording will also serve to detect any plugging of the exit conduit from the powder chamber. The flow rate at the inlet of the exposure line is monitored with a Fleisch pneumotachograph and a Validyne pressure transducer. The recording shows both the constant flow component induced by the vacuum source and the superimposed breathing pattern of the IPL. The exposure control function calculates and records the tidal volume of the breathing lung during the exposures. The particle concentration is measured in real time at the exposure manifold outlet by means of Casella Microdust Pro light dispersion instrument. The recording is used to study the exiting aerosol bolus in detail and to allow for limiting the aerosol exposure to a fraction of the existing bolus. Further, the particle size distribution of the generated aerosol is determined with a Marple cascade impactor, whereby the mass distribution is determined in size interval of approximately 0.5-12 micrometers. The cascade impactor is placed at the position of the housing for the flow junction. The distance from the holding chamber to the first impactor stage is approximately the same as the distance from the holding chamber to the main bifurcation of the lungs during the exposures. The preparation of an aerosol exposure with system includes generating aerosols with approximately 100 ml air compressed to 20-160 bar. The powder in an amount of 0.1 to 5 mg is manually loaded to the powder chamber. The exposure flow rate is adjusted to the desired volume and passed through the bypass line. The events of the complete exposure cycle are controlled by the LabView equipment. The pressure chamber is pressurized by first switching valve V5 on and then immediately off. The aerosol generation is triggered by releasing the main valve of the aerosol generator. The aerosol generation begins immediately and the aerosol cloud is collected in the holding chamber. The main valve can be reset at any remaining overpressure in the pressure chamber. This decreases the volume of the driving gas added to the holding chamber during the later phase o decompression when little aerosol remains to be generated. At an adjustable delay time after triggering the high-pressure valve, the exposure flow is redirected from the bypass branch to the exposure branch by simultaneously opening valves V1 and V3, and closing valves V2 and V4. The duration of the exposure can be adjusted to a desired length. A suitable guidance value is the volume of the holding chamber divided with the exposure flow rate. At values considerably exceeding this number, the entire volume of aerosol will be eluted from the system. At the end of the predetermined exposure phase, the exposure flow will be switched back to the bypass branch. The valves V1 and V3 are closed, while valves V2 and V4 are opened and the exposure cycle is finished. During the aerosol generation phase of the exposure cycle, the pressure in the pressure chamber is continuously monitored and displayed on the software front panel. The pressure recording can be saved as a data file for further analysis.

The system admits are number of immediate advantages. There is no need for pre-impactors to remove larger aggregates. The substances can most often be used in neat form without the need to involve excipients or diluents in order to increase the delivered dose of respirable aerosol to the lungs. Therefore, a high target dose via inhalation can be accomplished in a short time span.

Description of the Projected Pulmonary Deposition, Aerosol Yield and Particle Size Distribution The first procedure of an inhalation exposure using a new study material is to determine the particle size distribution of the generated aerosol. A Marple cascade impactor is connected to the aerosol outlet from the generator. The same amount of material as planned for the exposures is placed in the powder chamber, and a constant flow rate of 2 L/min is passed through the bypass line to a vacuum source downstream of the impactor. The aerosol is generated and passed through the impactor. After generation the deposition on the impactor stages are measured gravimetrically and the MMAD and GSD for the aerosol are calculated. Once the particle size distribution has been determined a theoretical deposition fraction for the used species of lung and ventilation pattern can be calculated from any of a number of models published.

Then in order avoid range finding exposures using live animals and spending precious study material an inhalation filter set up is used to directly predict lung deposition of in particular electrostatic aerosols. The DustGun aerosol system is set up as during the exposures. Instead of the live animal or an isolated perfused lung an inhalation filter is placed at the end of tubing system that essentially mimics the tubing of the lung exposures down to a position where the exposure aerosol enters respiratory system of the test subject. The inhalation filter is connected to a mechanical ventilator that simulates the ventilation pattern of the test subject during the duration of the aerosol exposure. Using a loop with two one-way valves only the inhaled aerosol passes the filter. The exhaled depleted air bypasses the filter in order to avoid resuspension of particles from the filter. The weight gain on the inhalation filter corresponds to the inhaled amount of material of the test subject during the exposures. After multiplication with the deposition fraction a much more accurate estimate of the lung-deposited dose can be obtained. The deposition fraction can be adjusted for an increased deposition of an electrostatic aerosol in the lungs. Simultaneously, deposition on the residual filter Mres is measured and used to correct the aerosol concentration recorded by the Casella instrument. Also, for each test exposure the ratio Minh/Mres is calculated.

TABLE 1

Overview of the most important results parameters from the exposures.

| Parameter | Name | Unit |
| --- | --- | --- |
| MMAD | Mass Median Aerodynamic Diameter | (μm) |
| GSD | Geometric Standard Deviation | (μm) |
| Fdep | Fraction Deposited | Dim less |
| Mres | Mass Deposition on Residual Filter | (μg) |
| Minh | Mass Inhaled on Exposure | (μg) |
| Mdep | Mass Deposited on Exposure | (μg) |

Two different estimates of the deposited dose during subject exposures can be calculated.

I. Deposition is calculated from the fractional deposition times the tidal volume times corrected aerosol concentration summed over all breaths of the exposure:

$Mdep = \Sigma Fdep \times TV \times Ccorr$

II Deposition is calculated from the ratio of inhalation/residual filter weights from the preexposure test times the residual filter weight of the exposure times the deposition fraction.

$Mdep = (Minh/Mres)_{test} \times Mres_{exp} \times Fdep$

Both estimates are calculated and compared. Accurate exposure estimates are important to achieve, particularly when a total mass balance of the study substance in the exposure subject cannot be obtained by quantitating the study substance in all tissues and excreta.

DESCRIPTION OF EMBODIMENTS

Figure 2A:
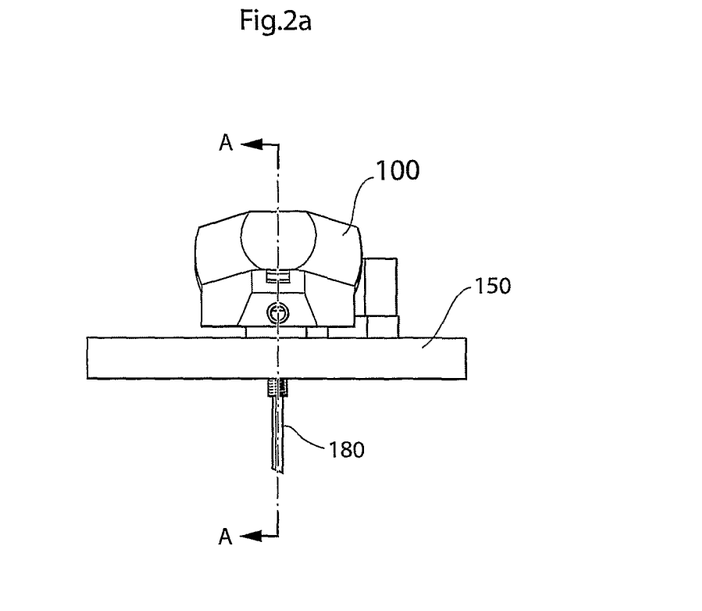
FIG. 2A is a side view of the filter device, the aerosol inlet device and the housing lid with aerosol connection means.
Figure 2B:
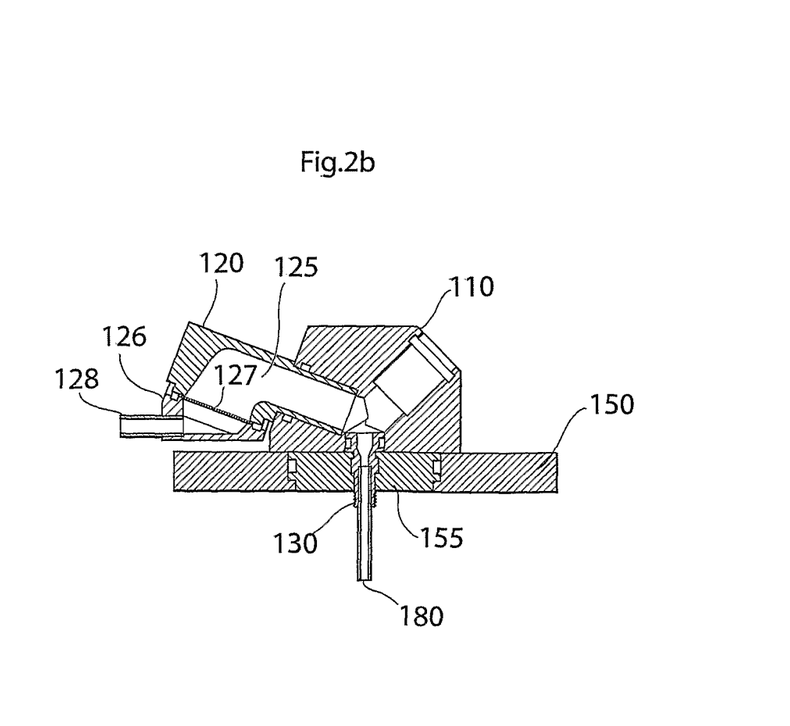
FIG. 2B is crossectional view of FIG. 2A along the line AA.

FIG. 2A generally shows the aerosol inlet device and the total filter device as integrated structure 100 sealingly attached to the lid part 150 of a housing which accommodates the exposure organ and is connected with a tubing 180. FIG. 2B is a crossectional view of the structure 100 along AA in FIG. 2A showing the aerosol inlet device with a generally tubular channel receiving an aerosol flow from the aerosol generator of the system described with FIG. 1. A nozzle generally designated 130 is arranged in a centrally located, detachable lid part 155 and is in connection with tubing 180 which in turn can be connected to the exposure organ (not shown) with a catheter or a similar device. The exposure organ, as exemplified with an isolated, ventilated and perfused lung accommodated in the housing (not shown) inhales from the aerosol flow received from the aerosol inlet device 110 through the nozzle 130, while also performing exhalations. Aerosol not consumed through the nozzle 130 will enter the filter device 120 which is provided with a tubular channel receiving a residual aerosol flow and a downstream filter chamber 125. The filter chamber 125 is provided with a detachable filter holder 126 for a residual filter 127 and an exit conduit 128 which is connection with an upstream vacuum source (not shown) capable of generating a controlled flow the through filter chamber. The filter chamber 125 and the inlet device are generally arranged to generate conditions that avoid losses of aerosol particles. For this purpose, the tubular channel extends in an angle of 45 degrees from the plane of residual filter, and the residual filter surface is essentially horizontal to retain deposited particles by gravity.

Figure 3:
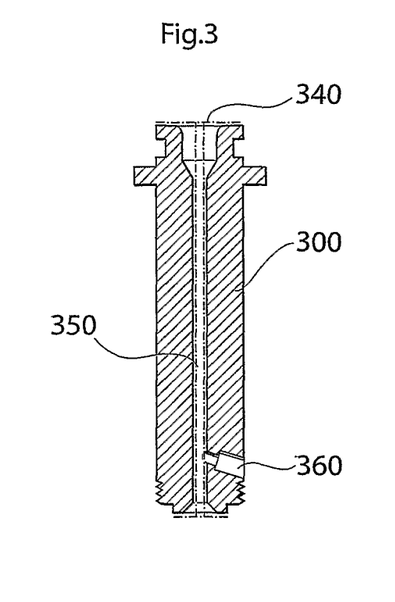
FIG. 3 is a crossectional view of the inhalation filter.

FIG. 3 shows a specially arranged inhalation filter 300 in cross-section which is designed to replace the centrally located, detachable lid part 155 and the nozzle arrangement of FIG. 2A. The inhalation filter has a centrally located conduit 350 between the proximal and distal parts and between its inlet 340 receiving aerosol from the inlet device depicted in FIG. 2A and the proximal part provided with means 360 to connect a deposition filter (not shown). The length of the conduit between the junction point and the filter is adapted to represent the length between the junction point and the lung in an arrangement when the system is run with a test animal. The conduit of the inhalation device and the tubular channel of the inlet device of FIG. 2A are arranged in angle of 45 degrees in order to optimize flowing conditions and minimize losses of aerosolized particles.

Figure 4A:
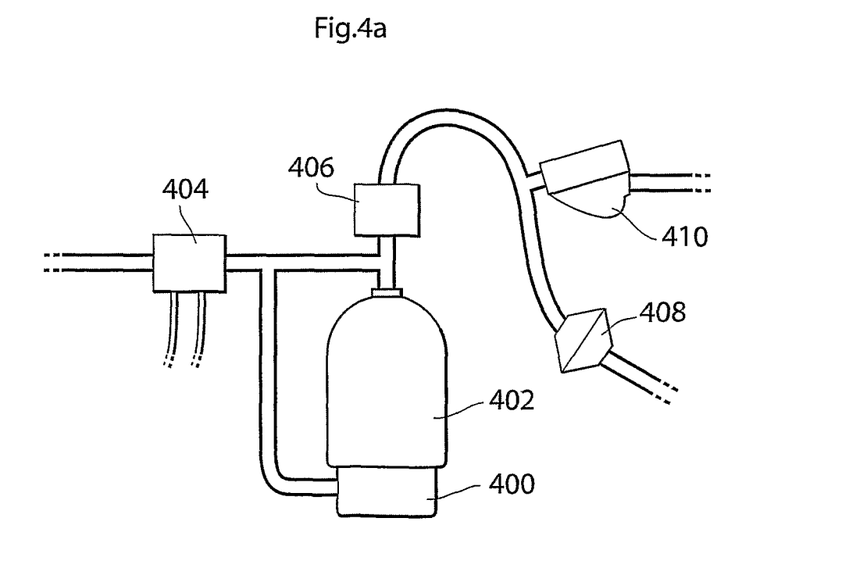
FIGS. 4A, B and C are schematic representations of three main exposure configurations
Figure 4B:
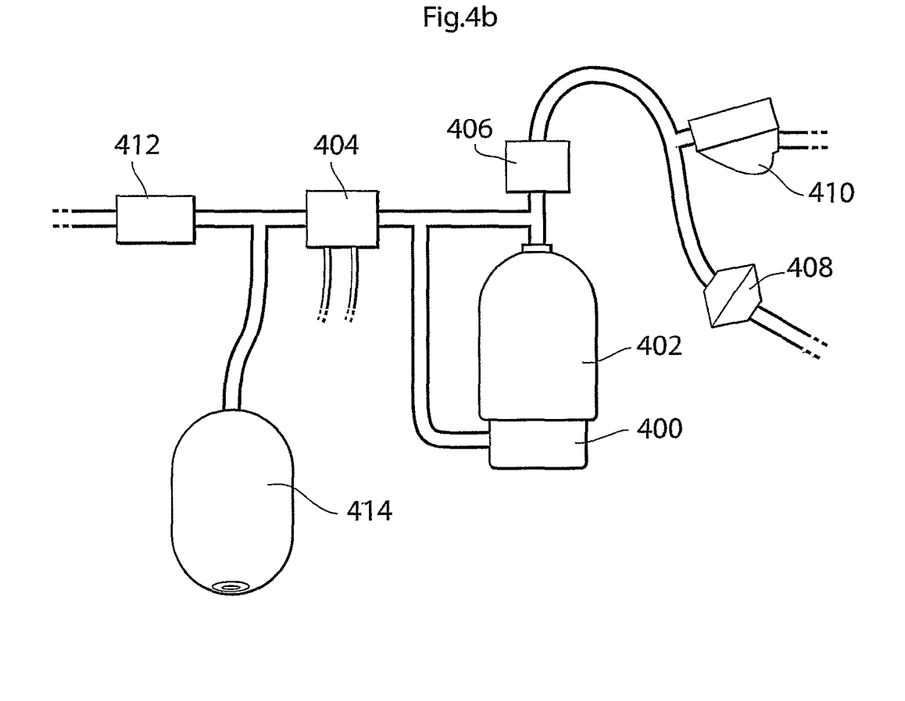
Figure 4C:
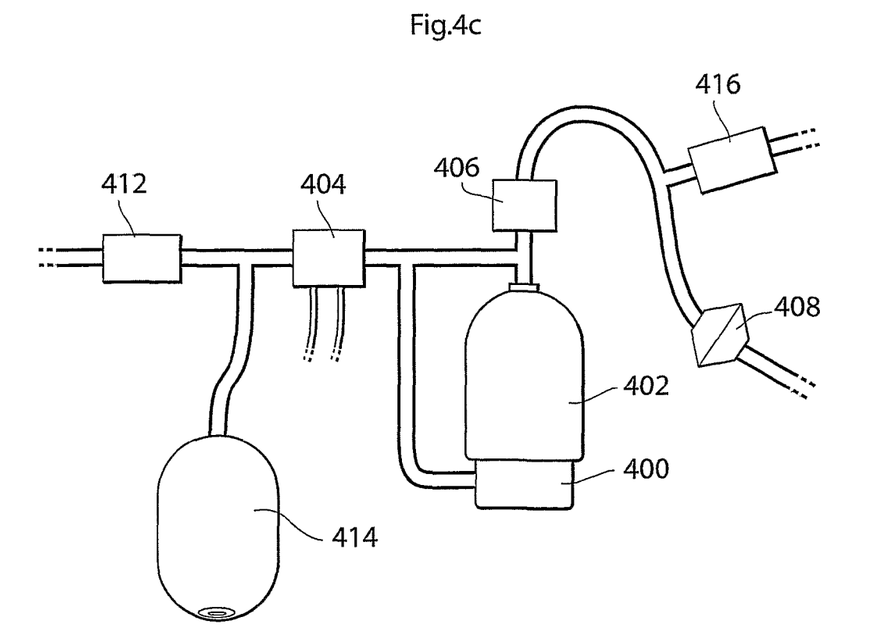

FIGS. 4A to C illustrate schematically three different modes of running the inventive system for précising the aerosol dose delivered to the lung. The systems of FIGS. 4A to C have a DustGun aerosol generator with an aerosol holding chamber which is opened following aerosol generation to provide an aerosol flow to the exposure line. The systems have a pneumotachometer in the beginning of the exposure flow line and a Casella instrument located downstream in the flow line before a junction point from which an exposure flow is taken from the transportation flow to inhalation filter coupled to a breathing simulator (not shown), leaving a residual flow. FIG. 4A shows a system adapted for small lungs having a maximum ventilation flow Qvent less than the transport aerosol flow in the exposure flow line Qexp. In this case, the breathing simulator provides a tidal volume (TV) that is less than the volume of holding chamber Vchamber and the transportation flow is generated by a vacuum source. A relatively small amount of aerosolized particles will be deposited in the inhalation filter compared to the filter in the residual flow line. FIG. 4B illustrates a system arrangement adapted for the study of medium sized lungs with Qvent exceeding the exposure flow in the flow line (Qexp), but with tidal volume less than the volume of the holding chamber. In order to ensure a correct flow and not lose aerosol from the system, this arrangement is provided with a one-way valve and ventilation balloon located upstream the pneumotachometer in the exposure flow line. FIG. 4C shows a system arranged for the study of large lungs with a tidal volume exceeding the volume of the aerosol holding chamber. In this embodiment, it is contemplated that most of the aerosol dose will be consumed by the animal, so in comparison with the arrangement of FIG. 4B, it does not have a filter device in the residual flow, but a second one-way valve downstream in the residual flow considering the large quantities of exhaled and inhaled air, so a correct flow can be maintained in the system.

Figure 5:
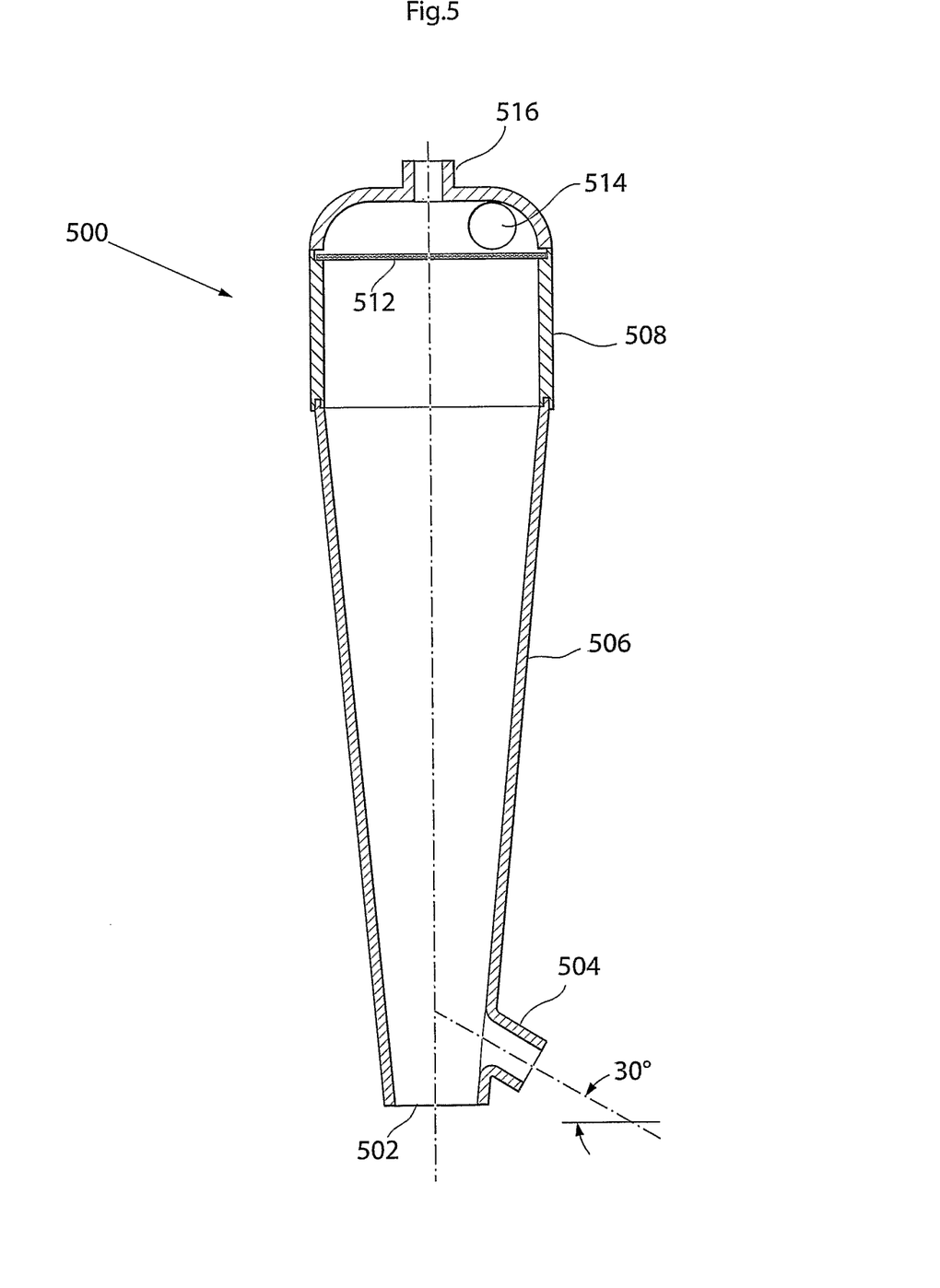
FIG. 5 is a crossectional view of the holding chamber according to the present invention

FIG. 5 shows a schematic cross-sectional view of an aerosol holding chamber 500 adapted to accommodate an aerosol burst and transport an aerosol to an exposure target (not shown), having an inlet 502 and an outlet conduit 504. The inlet 502 is adapted to be connected to an aerosol generator (in FIG. 1 referred to as 10) for receiving an aerosol burst from the aerosol generator 10. The outlet conduit 504 is adapted to distribute an exposure aerosol flow to an exposure organ (not shown). The aerosol holding chamber 500 is adapted to be mounted vertically with its inlet 502 being downwardly directed. Furthermore, the aerosol holding chamber 500 is provided with a guide 516 on the top for fixating the aerosol holding chamber 500. The outlet conduit 504 extends in an angle of about 30 degrees downwardly from the horizontal plane. The aerosol holding chamber 500 is generally conically shaped, the top having a larger crossectional area than its bottom. The aerosol holding chamber 500 is divided in a lower compartment 506 and an upper compartment 508, being sealingly but releasingly connected with each other, the lower compartment 506 comprising the inlet 502 and the outlet conduit 504. Furthermore, the upper compartment 508 containing a perforated screen or mesh with or without a filter, comprises a diffuser 512 adapted to introduce clean particle-free air as a stable layer on top of the denser aerosol. The diffuser 512 is located in the top of the upper compartment 508 and comprises a clean air inlet 514 and a perforated screen/disc. However, a person skilled in the art will understand that any other suitable diffuser might be used in the manner described.

Figure 6:
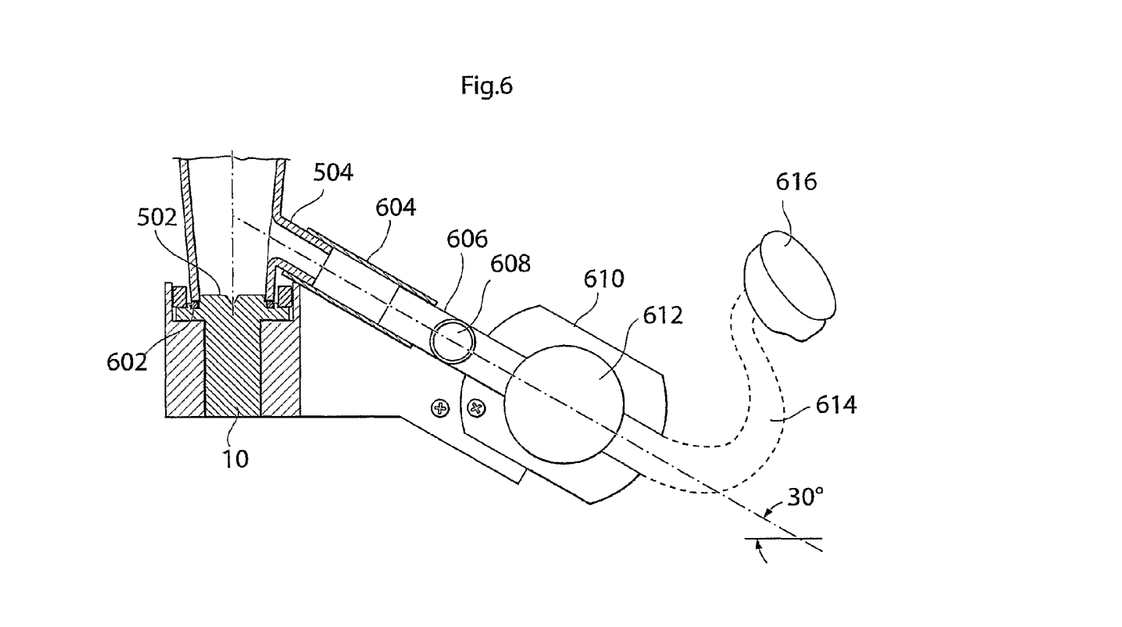
FIG. 6 shows the holding chamber with the outlet conduit.

FIG. 6 shows a schematic crossectional view of the bottom part of the aerosol holding chamber 500, where the inlet 502 and the outlet conduit 504 (both referring to FIG. 5) are provided. The inlet 502 is adapted to be connected to an aerosol generator (in FIG. 1 referred to as 10) for receiving an aerosol burst from the aerosol generator 10. The aerosol generator 10 is provided with a packing ring 602 to provide a sealingly connection with the inlet 502. Aerosol removal from the holding chamber 500 to exposure subject is controlled with two pinch valves and a bypass line 606. In the exposure configuration the exposure subject are exposed to aerosol via the outlet conduit 504 and an open pinch valve acting on the tube at 604. The bypass-line 608 feeding aerosol-free air to the exposure subject via the T-coupling 606 is then closed with a pinch valve not shown. In the bypass configuration the exposure subject is exposed to aerosol-free air via the bypass line 608 with an open pinch valve, at which the pinch valve of the exposure line is closed at 604. Although pin valves are applied in this exemplary embodiment, a person skilled in the art will understand that any other suitable valves might be used in the manner described.

The holder 610 is provided with a cavity 612, adapted to hold the aerosol measuring instrument, which will measure the aerosol concentration of the mixture of aerosol and fresh air. The holder 610 is further provided with an outlet, adapted to transport the mixture of aerosol and fresh air via a respiratory tubing 614 to an exposure organ 616.

Figure 7:
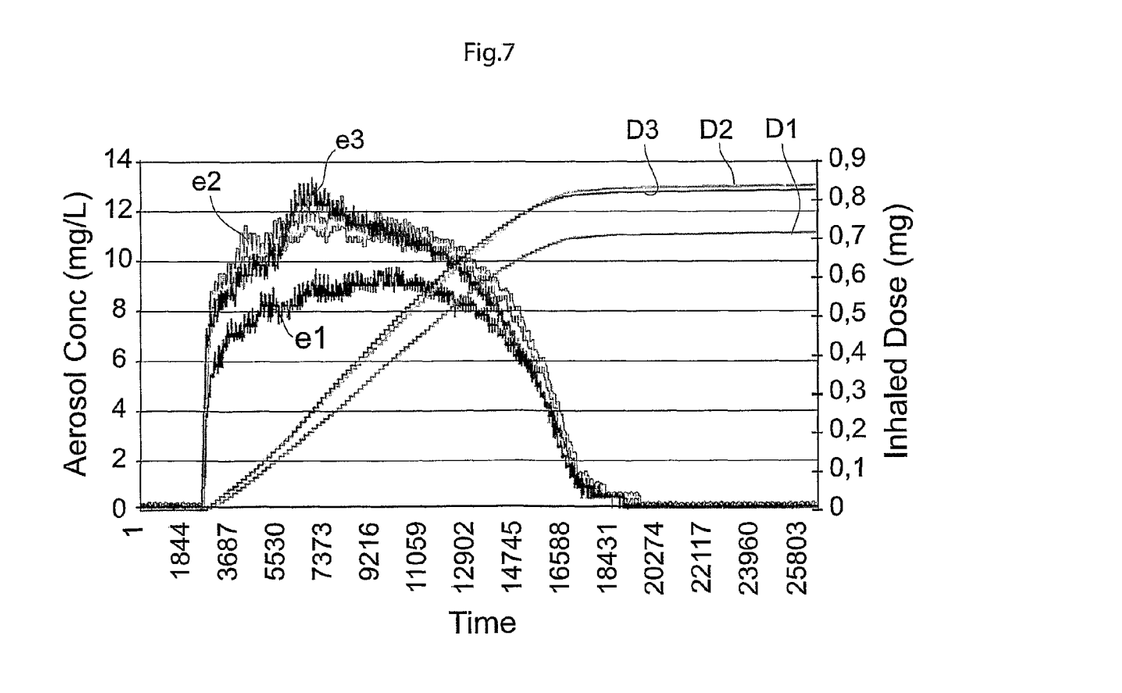
FIG. 7 shows graphs from exposure system experiments with horseradish peroxidase.

FIG. 7 shows three different tests with micronized dry horseradish peroxidase (HRP) in the amounts of 2.21; 2.65 and 2.68 mg aerosolized HRP for exposures with an IPL by the system shown in FIG. 1 and described above. FIG. 7 shows curves (e1 to e3) showing aerosol particle concentration measured with a Casella instrument recorded 100 times per second. The curves D1 to D3 show the inhaled dose prospected from these volume when considering the tidal volume (breathing characteristics) of the IPL. The different curves exhibit an excellent correlation between the different exposures . . . .

Figure 8:
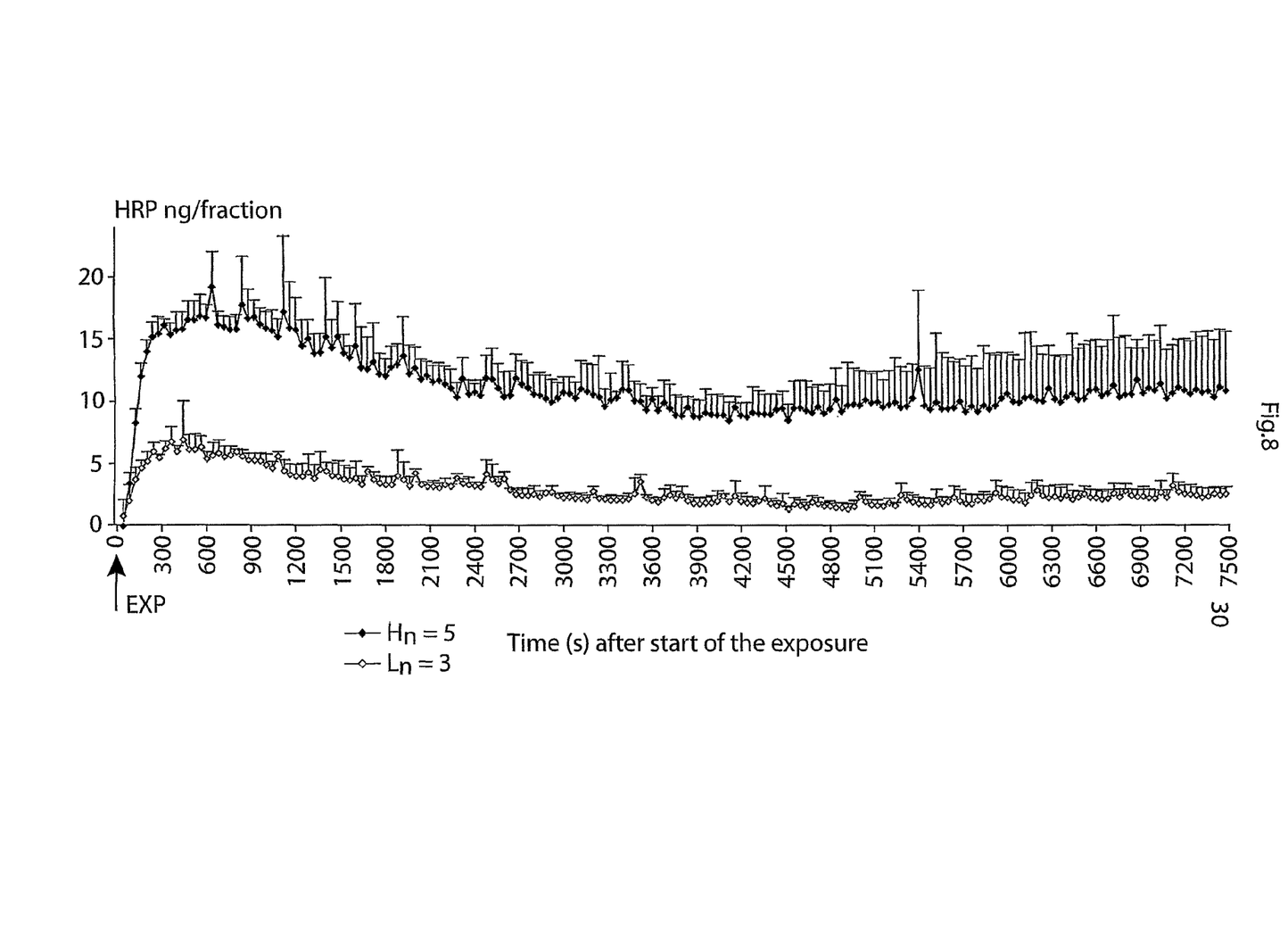
FIG. 8 shows a graph of the amount of horseradish peroxidase in the perfusates from two different exposures of an IPL.
Figure 9:
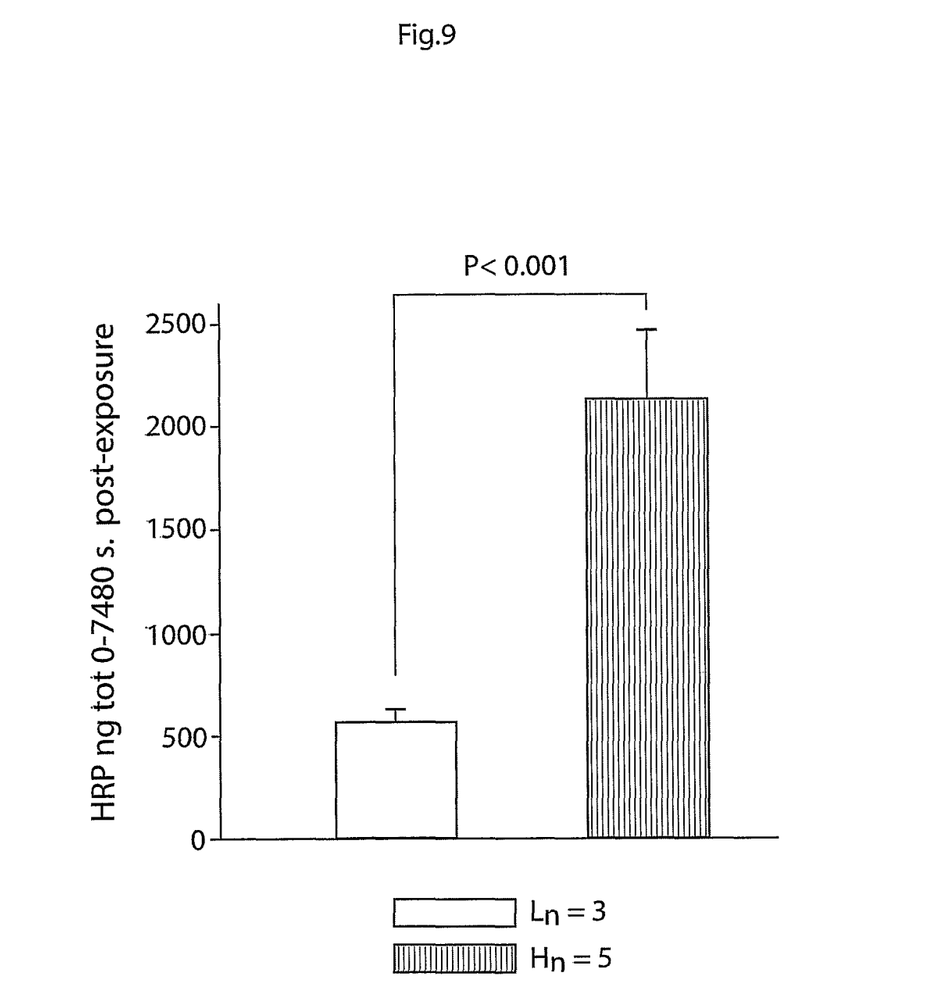
FIG. 9 shows a graph of the cumulative amount of horseradish peroxidase of the perfusates shown in FIG. 8 over the total time of the perfusion periods.

FIG. 8 shows the amount of HRP in the perfusates from two different exposures of an IPL with one higher and one lower level of HRP. Fractions of perfusate were collected each 40s. FIG. 9 shows the cumulative amount of HRP of the perfusates shown in FIG. 9 over the total time of the perfusion periods. It is evident from these results that the system provides a low variability between different exposures although low amount aerosolized test compounds were used.

The invention claimed is:

1. A method of transporting an aerosol bolus from an aerosol generator to an exposure target comprising the steps of
   (a) introducing an upwardly directed burst of aerosol from the aerosol generator in the bottom part of a generally vertically oriented holding chamber having a shape adapted to accommodate the volume of bursted aerosol;
   (b) allowing the aerosol to settle and collect as a cloud by means of gravitation in said holding chamber;
   (c) introducing a layer of lighter clean air over said denser aerosol cloud; and
   (d) receiving an aerosol stream in a downwardly directed outlet conduit of the holding chamber for transportation to the exposure target.

2. A method according to claim 1, wherein the holding chamber has the shape of an inverted cone.

3. A method according to claim 1 comprising preventing unstable mixing of the aerosol and the clean air during the exposure maneuver.

4. A method of transportation according to claim 1, wherein the outlet conduit is located in a bottom part of the holding chamber.

5. A method of transportation according to claim 1, wherein the transportation of the aerosol from the holding chamber to the exposure target is performed by gravitation.

6. A method of transportation according to claim 1 comprising the settling of a denser aerosol as a cloud in the holding chamber so it reaches a stable boundary towards the lighter clean air above.

7. A method according to claim 1, wherein the clean air exerts a pressure on the aerosol cloud, thereby supporting its displacement from the holding chamber.

8. A method of transportation according to claim 1 in an exposure system wherein the aerosol generator is sealingly connected to an exposure arrangement adapted to provide:
   a transport aerosol flow from an aerosol holding chamber of the aerosol generator to a flow junction;
   an exposure aerosol flow from the flow junction for distribution to an exposure organ with breathing capacity thereby a providing a residual aerosol flow transported away from the flow junction, said exposure arrangement further comprises:
   a flow rate monitoring device located upstream the flow junction for monitoring the transport aerosol flow;
   a device for measuring the aerosol particle concentration located downstream the flow rate monitoring device;
   and optionally a flow control function for controlling the transport aerosol flow.

9. A aerosol holding chamber for accommodation of an aerosol burst and transportation of an aerosol to an exposure target characterized in that the chamber is essentially vertically extended between a top of the aerosol holding chamber and a bottom of the aerosol holding chamber, said top having a larger crossectional area than said bottom providing the chamber with the general configuration of an inverted cone, wherein said bottom has (i) an aerosol inlet adapted to receive an upwardly directed burst of an aerosol bolus from the aerosol generator; and separately (ii) an aerosol outlet conduit for receiving the aerosol for transportation to the exposure target.

10. An aerosol holding chamber according to claim 9 comprising a valve function for opening the outlet conduit for transportation.

11. An aerosol holding chamber according to claim 9, wherein the outlet conduit is downwardly directed.

12. An aerosol holding chamber according to claim 9 having a diffuser located in the top for introducing clean particle-free air as a stable layer on top of the denser aerosol.

13. An aerosol holding chamber according to claim 7, wherein the aerosol holding chamber comprises a lower compartment and an upper compartment being sealingly but releasingly connected with each other, the lower compartment being provided with the aerosol inlet and the aerosol outlet conduit.

14. A system comprising an aerosol generator, the aerosol holding chamber of claim 9, and conduits for transporting an aerosol flow from the aerosol holding chamber to a flow junction, for transporting an exposure aerosol flow from the flow junction for distribution to an exposure target, and for providing a residual aerosol flow transported away from the flow junction.

15. A system according to claim 14, further comprising a flow rate monitoring device located upstream of the flow junction for monitoring the transport aerosol flow.

16. A system according to claim 15, further comprising a device for measuring aerosol particle concentration located downstream of the flow rate monitoring device.

\* \* \* \* \*